United States Patent

Sala et al.

Patent Number: 5,376,673
Date of Patent: Dec. 27, 1994

[54] ISOINDOLES HAVING CARDIOVASCULAR ACTIVITY

[75] Inventors: Alberto Sala; Silvio Levi; Francesca Benedini; Roberta Cereda; Piero Soldato, all of Milan, Italy

[73] Assignee: Italfarmaco S.p.A., Milan, Italy

[21] Appl. No.: 117,162

[22] Filed: Sep. 17, 1993

[30] Foreign Application Priority Data

Mar. 19, 1991 [IT] Italy ............................ MI91A000732

[51] Int. Cl.$^5$ ...................... A61K 31/40; C07D 209/48
[52] U.S. Cl. ........................ 514/417; 548/477
[58] Field of Search .................... 514/417; 548/477

[56] References Cited

U.S. PATENT DOCUMENTS 5,189,034  2/1993  Sala et al. ..................... 514/224.2

FOREIGN PATENT DOCUMENTS 0171977  2/1986  European Pat. Off. .

OTHER PUBLICATIONS

Chemical Abstracts, vol. 108, No. 21, May 23, 1988, Columbus, Ohio, US; abstract No. 186566R, Y. Morisawa: "Preparation of Phthlimidines for Treatment of Angina Pectoris", p. 688.

Primary Examiner—Mary C. Lee
Assistant Examiner—Jacqueline Haley
Attorney, Agent, or Firm—Oblon, Spivak, McClelland, Maier, & Neustadt

[57] ABSTRACT

Isoindole compounds of the formula (I)

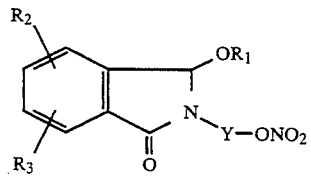

wherein $R_1$ represents hydrogen; $C_1$–$C_6$ alkyl; benzyl optionally substituted with halogen, hydroxy, $C_1$–$C_6$ alkoxy, methylenedioxy; $C_2$–$C_8$ aliphatic acyl; benzoyl optionally substituted with halogen, hydroxy, $C_1$–$C_6$ alkoxy, $C_2$–$C_6$ alkanoyl, $C_2$–$C_6$ alkanoyloxy, $C_1$–$C_4$ alkyl, trifluoromethyl, methylenedioxy;

$R_2$–$R_3$ are selected independently from hydrogen; halogen; $C_1$–$C_4$ alkyl; trifluoromethyl; hydroxy; nitro; amino; mono or di $C_1$–$C_4$ alkylamino; cyano; $C_1$–$C_6$ alkoxy; $C_2$–$C_6$ alkoxycarbonyl;

Y is ethylene, or a straight or branched alkylene chain containing from 3 to 6 carbon atoms, and the salts thereof of pharmaceutically acceptable acids. The compounds possess antianginal activity and are used in the preparation of medicaments for antianginal therapy.

3 Claims, No Drawings

ISOINDOLES HAVING CARDIOVASCULAR ACTIVITY

The present invention relates to isoindoles having cardiovascular activity, a process for the preparation thereof and pharmaceutical compositions containing them.

The compounds of the invention have the following general formula:

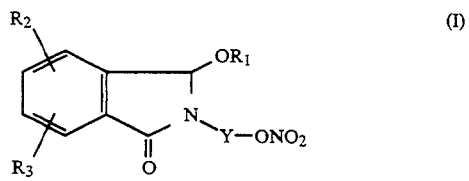

wherein:

$R_1$ is selected from hydrogen; $C_1-C_6$ alkyl; benzyl optionally substituted with halogen, hydroxy, $C_1-C_6$alkoxy, methylenedioxy; $C_2-C_8$ aliphatic acyl; benzoyl optionally substituted with halogen, hydroxy, $C_1-C_6$ alkoxy, $C_2-C_6$ alkanoyl, $C_2-C_6$ alkanoyloxy, $C_1-C_4$ alkyl, trifluoromethyl, methylenedioxy;

$R_2$ and $R_3$ are selected independently from hydrogen; halogen; $C_1-C_4$ alkyl; trifluoromethyl; hydroxy; nitro; amino; mono or di $C_1-C_4$ alkylamino; cyano; $C_1-C_6$ alkoxy; $C_2-C_6$ alkoxycarbonyl;

Y is ethylene, or a straight or branched alkylene chain containing from 3 to 6 carbon atoms.

A further object of the invention is provided by the salts of compounds of formula (I) with pharmaceutically acceptable acids.

3-Substituted 1-oxo-isoindoles bearing a nitrooxyalkylene chain as the substituent, whether the chain is linked to the nitrogen atom or not, are not known from literature, including the patent one. On the contrary, phthalimido derivatives having coronary dilating activity, in which derivatives the nitrogen atom is substituted by a nitrooxyalkylene group, are known from EP-A-171.977. Moreover, phthalimidines substituted at the nitrogen atom by a nitrooxyalkylene chain having antianginal activity, are known from C.A. 108, 186566t, page 688.

As stated above, the compounds of the invention have cardiovascular activity. Particularly, they were found to have high in vitro vasorelaxing activities and a marked antianginal activity in the laboratory animal. Besides having such favourable biological activities, said compounds have a negligible hypotensive effect, which is known to be an undesired side-effect of the up-to-now known and used nitro-derivatives.

Therefore, the compounds of the invention could be used as antianginal agents.

They also proved to have antiarrhytmic activity, which is another favourable feature since angina attacks are often accompanied by more or less marked arrhytmias.

The compounds of the invention can be prepared according to the following scheme 1:

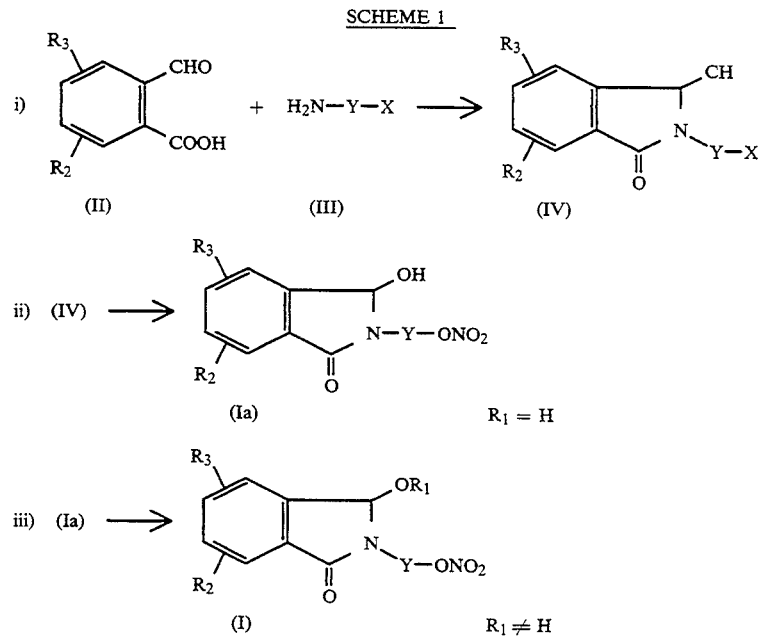

wherein X is halogen, whereas Y, $R_2$ and $R_3$ are as defined above, and $R_1$ has the meanings defined for scheme 1.

The starting compound, 2-carboxybenzaldehyde of formula II in which the carboxy group has previously been activated, is reacted with a haloalkylamine (III) to give the product (IV); substitution of halogen X with a nitrooxy group by reaction with AgNO₃ yields to compounds (Ia). Compounds (I) in which $R_1$ is different from H, can be obtained by acylation or alkylation or benzylation of compounds (Ia) according to conventional methods.

Step i) is carried out preferably in an inert solvent, such as, for example, an halogenated solvent, in the presence of an acid-binding agent, for example a suitable organic base. The reaction temperature is comprised between $-10°$ C. and $10°$ C., preferably between $0°$ C. and $5°$ C.

Step ii) is carried out in a polar organic solvent, such as acetonitrile, at the reflux temperature of the solvent.

Acylation of (Ia), according to step iii), can be carried out with acyl chlorides in the presence of a catalyst, such as dimethylaminopyridine, and a proton-binding agent, such as triethylamine; the reaction solvent is generally a poorly polar solvent, for example an open- or closed-chain ether, such as tetrahydrofuran.

Alkylation or benzylation of (Ia) according to step iii), on the contrary, can be carried out with suitable alkyl or benzyl halides in the presence of a strong base, for example sodium hydride or an alkali metal alkoxide, or by reacting the compound (Ia) with the selected alkanol or benzyl alcohol in the presence of strong acids.

When compounds of formula (I) are desired in which $R_2$ and $R_3$ are at the 5- and 6-positions and they are the same, an alternative preparation can be carried out according to the following scheme 2:

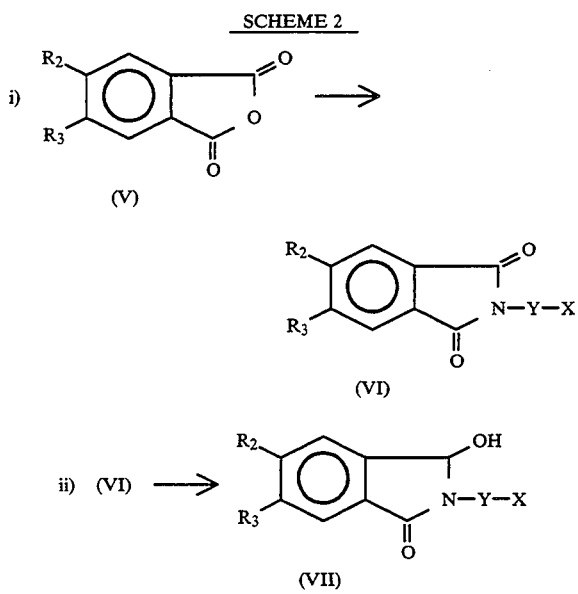

wherein X, Y, $R_2$ and $R_3$ are as defined above.

Phthalic anhydride of formula (V) is transformed into the corresponding phthalimide of formula (VI) by reaction with a ω-haloalkylamine of formula (III). Subsequently one of the phthalimide carbonyl groups is reduced to hydroxy by means of a suitable reducing agent, for example sodium bis-(2-methoxyethoxy)aluminium hydride (Red-Al), in a suitable organic solvent, such as toluene, to obtain the compound of formula (VII). The latter is then converted into the desired final products of formula (I) as described above. The reactive groups present in the aromatic ring can previously be protected according to conventional methods, with suitable substituents which can easily be removed to obtain the final products. Carboxyaldehydes of formula (II), ω-haloalkylamines of formula (III) and phthalic anhydrides of formula (V) are commercially available products or they are prepared according to known methods. Some phthalimides of formula (VI) are also commercial products and therefore they are used as such for the reduction of the above carbonyls.

$^1$H-NMR Spectra were recorded in dimethylsulfoxide (DMSO-d6) with a VARIAN GEMINI 200 spectrometer. $^{13}$C-NMR Spectra were recorded using a VARIAN GEMINI 200 spectrometer, taking the 39.5 p.p.m. peak of dimethylsulfoxide (DMSO-d6) as the reference peak.

The following examples further illustrate the invention.

EXAMPLE 1

3-Hydroxy-2-(2-nitrooxyethyl)-1-oxoisoindolin

A. 3-Hydroxy-2-(2-chloroethyl)-1-oxoisoindolin 9.7 ml (0.101 mole) of ethyl chlorocarbonate were dropwise added to a solution of 15.2 g (0.101 mole) of 2-carboxybenzaldehyde in 500 ml of chloroform and 14.1 ml (0.101 mole) of triethylamine, cooled to 0° C. After 45 minutes, a solution of 11.7 g (0.101 mole) of 2-chloroethylamine hydrochloride in 200 ml of chloroform and 14.1 ml (0.101 mole) of triethylamine was dropwise added thereto. The obtained solution was kept at 0°–5° C. for 5 hours. After warming to room temperature, the mixture was washed with water, 5% sodium bicarbonate, again with water and finally dried over sodium sulfate. 19 g of a crude product were obtained, which was purified on silica gel column eluting with methylene chloride-acetone 10/1 (v/v). 7 g of the title product were obtained; mp=133°–134° C. (methylene chloride).

B. 3-Hydroxy-2-(2-nitrooxyethyl)-1-oxoisoindolin

To a solution of 5 g (0.023 mole) of the product prepared in 1A in 150 ml of acetonitrile, 7.8 g (0.046 mole) of silver nitrate were added. The mixture was refluxed for 3 hours, shielded from light, then it was warmed to room temperature, the salts were filtered off and the solvent was evaporated off. The resulting crude product was taken up into methylene chloride, washed with water and dried over sodium sulfate. 6 g of the title product were obtained; mp=143°–145° C. (acetonitrile).

EXAMPLE 2

3-Acetoxy-2-(2-nitrooxyethyl)-1-oxoisoindolin

A solution of 17 g (0.070 mole) of the compound prepared in 1B and 440 mg (0.004 mole) of 4-dimethylaminopyridine in 6.7 ml (0.071 mole) of acetic anhydride and 9.9 ml (0.071 mole) of triethylamine was kept for 2 hours at room temperature under stirring. The mixture was taken up into methylene chloride, washed with 5% hydrochloric acid, water and finally dried over sodium sulfate. 23 g of crude product were obtained, which was purified on silica gel column eluting with methylene chloride-acetone 97/3 (v/v). 18 g of the title product were obtained; mp=74°–75° C. (hexane).

EXAMPLE 3

3-Butoxycarbonyl-2-(2-nitrooxyethyl)-1-oxoisoindolin

The compound was prepared as described in example 2, starting from 3.4 g (0.014 mole) of the compound prepared in 1B, 170 mg (0.0014 mole) of dimethylaminopyridine, 1.48 ml (0.014 mole) of n-butanoyl chloride and 1.95 ml (0.014 mole) of triethylamine. 2.27 g of the title product were obtained as an oil having the following characteristics:

| Elementary analysis: | % C | % H | % N |
|---|---|---|---|
| calculated | 54.54 | 5.23 | 9.09 |
| found | 54.11 | 5.25 | 9.00 |

¹HNMR (δ ppm, DMSO-d6) 7.80÷7.60 (m, 4H); 7.16 (s, 1H); 4.88÷4.64 (m, 2H); 4.07÷3.94 (m, 1H); 3.75÷3.63 (m, 1H); 2.78 (t, 2H) 1.61 (m, 1H) 0.92 (t, 3H). ¹³CNMR 173.51; 167.60; 141.69; 133.26; 131.10; 130.69; 124.47; 123.30; 81.41; 71.44; 38.01; 35.56; 18.00; 13.61.

EXAMPLE 4

3-Benzoyloxy-2-(5-nitrooxyethyl)-1-oxoisoindolin

The compound was prepared as described in example 2, starting from 2 g (0.008 mole) of the compound prepared in 1B, 51 mg (0.0004 mole) of dimethylaminopyridine, 1.14 ml (0.008 mole) of triethylamine and 0.95 ml (0.008 mole) of benzoyl chloride. 2.4 g of the title product were obtained; mp=65°-67° C. (hexane).

EXAMPLE 5

3-Hydroxy-2-(5-nitrooxypentyl)-1-oxoisoindolin

A. N-(5-Chloropentyl)phthalimide

A solution of 20.6 g (0.139 mole) of phthalic anhydride, 20 g (0.126 mole) of 5-chloropentylamine hydrochloride and 17.6 ml (0.126 mole) of triethylamine in 250 ml of toluene was heated to 130° C. for 4 hours. The obtained mixture was evaporated to dryness. The residue was taken up into 200 ml of water and extracted with ethyl acetate. The phases were separated and the organic phase was dried over sodium sulfate and evaporated to dryness. From the crude product, 23 g of the title product were obtained as an oil having the following characteristics:

| Elementary analysis: | % C | % H | % N | % Cl |
|---|---|---|---|---|
| calculate | 62.03 | 5.61 | 5.56 | 14.08 |
| found | 61.98 | 5.45 | 5.31 | 14.00 |

¹HNMR (ppm, DMSO-d6) 7.70÷7.61 (m, 4H); 3.80÷3.40 (m, 4H); 2.00÷11 (m, 6H) ¹³CNMR (ppm) 162.9; 149.9; 132.2; 129.9; 45.0; 44.9; 32.8; 28.4; 24.5.

B. 3-Hydroxy-2-(5-chloropentyl)-1-oxoisoindolin 22 g (0.087 mole) of the product prepared in 5A were dissolved in 200 ml of toluene and cooled to −20° C. 21.3 g (0.073 mole) of a 70% Red-Al solution in toluene diluted in 100 ml of toluene were dropwise added thereto. The obtained solution was kept at −20° C. for 2 hours. The solution was warmed to room temperature, then 300 ml of water were added thereto. The formed salts were filtered off and the phases were separated. The organic phase was dried over sodium sulfate and evaporated to give 13 g of the title product; mp=77°-79° C. (n-hexane).

C. 3-Hydroxy-2-(5-nitrooxypentyl)-1-oxoisoindolin

The product was prepared as described in 1B, starting from 10 g (0.039 mole) of the compound prepared in 5B. 5.8 g of the title product were obtained; mp=70°-72° C. (ethyl ether).

EXAMPLE 6

3-Acetoxy-2-(5-nitrooxypentyl)-1-oxoisoindolin

The compound was prepared as described in 2, starting from 8 g of the product prepared in 5C. 3 g of the title product were obtained as an oil having the following characteristics:

| Elementary analysis: | % C | % H | % N |
|---|---|---|---|
| calculated | 54.19 | 5.85 | 9.03 |
| found | 54.03 | 5.64 | 8.98 |

¹HNMR (δ ppm, DMSO-d6) 7.76÷7.58 (m, 4H); 7.07 (s, 1H); 4.52 (t, 2H); 3.69÷3.55 (m, 1H); 3.35÷3.21 (m, 1H) 2.16 (s, 3H); 1.78÷1.27 (m, 6H) ¹³CNMR 171.05; 167.23; 141.46; 132.87; 131.64; 130.60; 124.41; 123.08; 81.01; 73.97; 39.83; 27.51; 25.95; 22.74; 21.11.

EXAMPLE 7

3-Hydroxy-2-(2-nitrooxyethyl)-1-oxoisoindolin

A. 3-Hydroxy-2-(2-bromoethyl)-1-oxoisoindolin

The compound was prepared as described in 5B, starting from 250 g (0.098 mole) of N-(2-bromoethyl)phthalimide (commercial product). 8 g of the title product were obtained; mp=123°-124° C. (methylene chloride).

B. 3-Hydroxy-2-(2-nitrooxyethyl)-1-oxoisoindolin

The compound was prepared as described in 1B, starting from 7 g (0.027 mole) of the compound prepared in 7A. 5.3 g of the title product were obtained; mp=143°-145° C. (acetonitrile).

EXAMPLE 8

3-(2-Acetoxybenzoyl)-2-(2-nitrooxyethyl)-1-oxoisoindolin

A solution of 6.98 ml (0.050 mole) of triethylamine in 300 ml of acetonitrile was added with 5 g (0.025 mole) of acetylsalicylic acid chloride dissolved in 30 ml of acetonitrile and 5 g (0.021 mole) of the product prepared In 1B dissolved in 240 ml of acetonitrile-tetrahydrofuran 1/1 (v/v). The solution was left at room temperature for 24 hours. The formed salts were removed and the solvent was evaporated under vacuum. The resulting crude product was purified over silica gel, eluting with ethyl acetate-hexane 7-3 (v/v). 4.8 g of the title product were obtained; mp=81°-83° C. (ethyl ether).

EXAMPLE 9

5-Chloro-3-hydroxy-2-(2-nitrooxyethyl)-1-oxoisoindolin

A. 5-Chloro-3-hydroxy-2-(2-bromoethyl)-1-oxoisoindolin

The compound was prepared as described in example 1A, starting from 2.5 g (0.013 mole) of 4-chloro-2-carboxybenzaldehyde (Il farmaco, Ed. Sci 31, 691, 1976) and 2.76 g (0.013 mole) of 2-bromoethylamine hydrobromide. 1.05 g of the title product were obtained; mp=164°-168 ° C. (n-hexane).

B. 5-Chloro-3-hydroxy-2-(nitrooxyethyl)-1-oxoisoindolin

The product was prepared as described in example 1B, starting from 1 g (0.003 mole) of the product prepared in 9A and 1.19 g (0.007 mole) of silver nitrate. 0.86 g of the title product were obtained; mp=116°-118° C. (toluene).

EXAMPLE 10

5,6-Dichloro-3-hydroxy-2-(2-nitrooxyethyl)-1-oxoisoindolin

A. 4,5-Dichloro-N-(2-chloroethyl)-phthalimide

The compound was prepared as described in example 5A, starting from 14 g (0.065 mole) of 4,5-dichlorophthalic anhydride (Beilstein 4th Ed. vol. 17 System No 6143) and 7.51 g (0.065 mole) of 2-chloroethylamine monohydrochloride. 10.5 g of the title product were obtained; mp=144°-145° C. (ethyl acetate)

B. 5,6-Dichloro-3-hydroxy-2-(2-chloroethyl)-1-oxoisoindolin

The compound was prepared as described in example 5B, starting from 9 g (0.032 mole) of the product prepared in 10A. 6.2 g of the title product were obtained; mp=147°-149° C. (hexane).

C. 5,6-Dichloro-3-hydroxy-2-(2-nitrooxyethyl)-1-oxoisoindolin

The compound was prepared as described in example 5C, starting from 58 g (0.021 mole) of the product prepared in 10B. 2.2 g of the title product were obtained; mp=145°-147° C. (acetonitrile).

EXAMPLE 11

3-Hydroxy-2-(3-nitrooxypropyl)-1-oxoisoindolin

A. 3-Hydroxy-2-(3-bromopropyl)-1-oxoisoindolin

The compound was prepared as de scribed in 5B, starting from 25 g (0.093 mole) of N-(3-bromopropyl)phthalimide (commercial product). 24.3 g of the title product were obtained; mp=79° C. (methylene chloride).

B. 3-Hydroxy-2-(3-nitrooxypropyl)-1-oxoisoindolin

The compound was prepared as described in 1B, starting from 10 g (0.037 mole) of the product prepared in 11A. 3 g of the title product were obtained; mp=72°-74° C. (hexane/ether 8/2).

The following products were prepared according to the procedures described in the above Examples.

| —Y—ONO$_2$ | R$_1$ | R$_2$ | R$_3$ |
|---|---|---|---|
| 2-nitrooxyethyl | hydrogen | 7-trifluoromethyl | hydrogen |
| " | acetyl | 5-fluoro | 7-fluoro |
| " | " | 5-chloro | 4-methyl |
| " | " | 5-methoxy | 6-methoxy |
| " | hydrogen | 5-nitro | hydrogen |
| " | hexanoyl | 7-chloro | 5-nitro |
| 3-nitrooxypropyl | hydrogen | 5-cyano | hydrogen |
| " | " | 5-chloro | 7-chloro |
| 4-nitrooxybutyl | acetyl | 6-methyl | 4-fluoro |
| " | hydrogen | 5-nitro | hydrogen |
| " | benzoyl | 5-ethyl | " |

The activity of the compounds of the invention on the cardiocirculatory system was evidenced in the following tests.

In vitro vasorelaxing activity

The vasorelaxing activity of the compounds of the invention was determined on rabbit aorta which had been contracted with noradrenaline, according to the method described in Eur. J. Pharmacol, 141, 195 (1987). The values are reported in the following table 1.

TABLE 1

| In vitro vasorelaxing activity | |
|---|---|
| Compound of Ex. N. | IC$_{50}$ (mole/l) |
| 1 | 1.3 10$^{-6}$ |
| 2 | 1.2 10$^{-6}$ |
| 3 | 2.4 10$^{-6}$ |
| 4 | 3.2 10$^{-6}$ |

TABLE 1-continued

| In vitro vasorelaxing activity | |
|---|---|
| Compound of Ex. N. | IC$_{50}$ (mole/l) |
| 5 | 1.3 10$^{-5}$ |

IC$_{50}$ = concentration of active substance, expressed in mole/liter, able to inhibit by 50% the contraction of the aorta "strip" induced by noradrenaline.

In vivo antianginal activity

The in vivo antianginal activity was evidenced on Sprague Dawley anaesthetized rats, weighing 350–400 g, operating according to the procedure of M. Leitold et al., Arzneim. Forsch. 36, 1454, 1986. The test was carried out administering the animal intravenously with 1 I. U./kg, equivalent to 3 mg/kg of Arg-vasopressin, which induces a coronary spasm which can be reproduced and evidenced electrocardiographycally with an increase in the amplitude of the T wave. The compounds of the invention were admininistered by gastric gavage at a dose of 3 mg/kg, 1 hour before administration of Argvasopressin. The antianginal effect was expressed as percent inhibition of the T wave increase versus controls.

The obtained results for some representative compounds of the invention are reported in Table 2.

TABLE 2

| Vasopressine angina in the anaesthetized rat | | |
|---|---|---|
| Product | mg/kg | Effect (%) |
| Ex. n. 1 | 3 | −56.1 |
| Ex. n. 3 | 3 | −55.2 |
| Ex. n. 4 | 3 | −34.5 |

The compounds of the invention, besides having the above reported favourable properties, also show a low toxicity: the LD$_{50}$ values, determined according to the method of Lichtfield and Wilcoxon, J. Pharm. Expt. Ther. 96, 99, 1949, are in fact higher than 500 mg/kg i.p. in the mouse and 800 mg/kg per os in the rat. Therefore, the present invention also relates to the use of the compounds of the invention as antianginal agents, as well as to all the industrial aspects connected to said use, including the pharmaceutical compositions containing the compounds of the invention. Examples of said compositions are tablets, dragees, syrups and vials, the latter being suitable for both the oral and the intramuscular or intravenous administrations. Said compositions will contain the active ingredient alone or in admixture with conventional carriers and excipients.

The dosages of the active ingredient can vary within a wide range, depending on the used compounds as well as the severity of the condition to be treated and the age and weight of the patient, as to obtain the best effect during 24 hours.

We claim:

1. A compound of the formula:

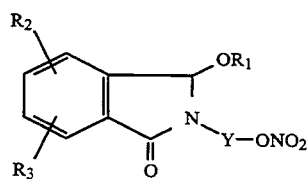

wherein:

$R_1$ is selected from hydrogen; $C_1$–$C_6$ alkyl; benzyl optionally substituted with halogen, hydroxy, $C_1$–$C_6$ alkoxy, methylenedioxy; $C_2$–$C_8$ aliphatic acyl; benzoyl optionally substituted with halogen, hydroxy, $C_1$–$C_6$ alkoxy, $C_2$–$C_6$ alkanoyl, $C_2$–$C_6$ alkanoyloxy, $C_1$–$C_4$ alkyl, trifluoromethyl, methylenedioxy;

$R_2$ and $R_3$ are selected independently from hydrogen; halogen; $C_1$–$C_4$ alkyl; trifluoromethyl; hydroxy; nitro; amino; mono or di $C_1$–$C_4$ alkylamino; cyano; $C_1$–$C_6$ alkoxy; $C_2$–$C_6$ alkoxycarbonyl;

Y is ethylene, or a straight or branched alkylene chain containing from 3 to 6 carbon atoms, and the salts thereof with pharmaceutically acceptable acids.

2. A pharmaceutical composition containing a therapeutically effective amount of a compound as defined in claim 1, in admixture with a pharmaceutically acceptable carrier.

3. A method of inhibiting the effects of angina in a mammal comprising administering to the mammal a therapeutically effective amount of a compound as defined in claim 1.

* * * * *

UNITED STATES PATENT AND TRADEMARK OFFICE
CERTIFICATE OF CORRECTION

PATENT NO. : 5,376,673
DATED : December 27, 1994
INVENTOR(S) : Alberto SALA, et al.

It is certified that error appears in the above-indentified patent and that said Letters Patent is hereby corrected as shown below:

On the title page, Items [22], [86], and [87], the PCT information has been omitted. It should read:

--[22] PCT Filed: Mar. 11, 1992

[86] PCT No.: PCT/EP92/00531
      § 371 Date: Sep. 17, 1993
      § 102 (e) Date: Sep. 17, 1993

[87] PCT Pub. No.: WO92/16506
      PCT Pub. Date: Oct. 1, 1992--

Signed and Sealed this

Twenty-fifth Day of April, 1995

Attest:

BRUCE LEHMAN

*Attesting Officer*     *Commissioner of Patents and Trademarks*